(12) United States Patent
Bradley (10) Patent No.: US 9,731,115 B2
(45) Date of Patent: Aug. 15, 2017

(54) SYSTEM AND METHOD FOR MUSCLE RECONDITIONING AND NEURAL REHABILITATION

(71) Applicant: BOSTON SCIENTIFIC NEUROMODULATION CORPORATION, Valencia, CA (US)

(72) Inventor: Kerry Bradley, Glendale, CA (US)

(73) Assignee: BOSTON SCIENTIFIC NEUROMODULATION CORPORATION, Valencia, CA (US)

(*) Notice: Subject to any disclaimer, the term of this patent is extended or adjusted under 35 U.S.C. 154(b) by 844 days.

(21) Appl. No.: 13/958,345

(22) Filed: Aug. 2, 2013

(65) Prior Publication Data

US 2014/0039574 A1 Feb. 6, 2014

Related U.S. Application Data

(60) Provisional application No. 61/679,712, filed on Aug. 4, 2012.

(51) Int. Cl.
*A61N 1/00* (2006.01)
*A61N 1/05* (2006.01)
*A61N 1/36* (2006.01)

(52) U.S. Cl.
CPC ....... *A61N 1/0551* (2013.01); *A61N 1/36071* (2013.01); *A61N 1/36171* (2013.01); *A61N 1/36175* (2013.01); *A61N 1/36185* (2013.01)

(58) Field of Classification Search
CPC ..... A61N 1/18; A61N 1/0551; A61N 1/36071
USPC ........................... 607/2, 45–48, 60, 116, 119
See application file for complete search history.

(56) References Cited

U.S. PATENT DOCUMENTS

| | | | |
|---|---|---|---|
| 4,712,558 A * | 12/1987 | Kidd et al. | 607/48 |
| 5,358,513 A * | 10/1994 | Powell et al. | 607/48 |
| 6,895,280 B2 | 5/2005 | Meadows et al. | |
| 7,650,184 B2 | 1/2010 | Walter | |
| 8,019,439 B2 | 9/2011 | Kuzma et al. | |
| 8,412,345 B2 | 4/2013 | Moffitt | |
| 2003/0120323 A1* | 6/2003 | Meadows et al. | 607/46 |
| 2007/0150036 A1* | 6/2007 | Anderson | 607/116 |
| 2007/0168004 A1 | 7/2007 | Walter | |
| 2007/0168007 A1* | 7/2007 | Kuzma et al. | 607/116 |
| 2011/0106215 A1 | 5/2011 | Moffitt | |

* cited by examiner

*Primary Examiner* — Nadia A Mahmood
(74) *Attorney, Agent, or Firm* — Faegre Baker Daniels LLP (57) ABSTRACT

A method for treating a patient requiring conditioning of one or more muscle groups comprises applying electrical stimulation to a ventral epidural space of the patient, thereby activating the muscles. The method includes conveying the stimulation energy to one or more motor efferents associated with the muscles through respective one or more electrodes implanted within the ventral epidural space, and thus activating the muscles.

21 Claims, 8 Drawing Sheets

SYSTEM AND METHOD FOR MUSCLE RECONDITIONING AND NEURAL REHABILITATION

RELATED APPLICATION DATA

The present application claims the benefit under 35 U.S.C. §119 to U.S. provisional patent application Ser. No. 61/679,712, filed Aug. 4, 2012. The foregoing application is hereby incorporated by reference into the present application in its entirety.

FIELD OF THE INVENTION

The present invention relates to tissue stimulation systems, and more particularly, to spinal cord stimulation systems.

BACKGROUND OF THE INVENTION

Implantable neurostimulation systems have proven therapeutic in a wide variety of diseases and disorders. For example, Spinal Cord Stimulation (SCS) techniques, which directly stimulate the spinal cord tissue of the patient, have long been accepted as a therapeutic modality for the treatment of chronic neuropathic pain syndromes, and the application of spinal cord stimulation has expanded to include additional applications, such as angina pectoralis, peripheral vascular disease, and incontinence, among others. Spinal cord stimulation is also a promising option for patients suffering from motor disorders, such as Parkinson's Disease, Dystonia and essential tremor.

An implantable SCS system typically includes one or more electrode-carrying stimulation leads, which are implanted at a stimulation site in proximity to the spinal cord tissue of the patient, and a neurostimulator implanted remotely from the stimulation site, but coupled either directly to the stimulation lead(s) or indirectly to the stimulation lead(s) via a lead extension. The neurostimulation system may further include a handheld patient programmer to instruct the neurostimulator remotely for generating electrical stimulation pulses in accordance with selected stimulation parameters. The handheld programmer may, itself, be programmed by a technician attending the patient, for example, by using a Clinician's Programmer (CP), which typically includes a general purpose computer, such as a laptop, with a programming software package installed thereon.

Thus, applied programmed electrical pulses can be delivered from the neurostimulator to the stimulation lead(s) to stimulate or activate a volume of the spinal cord tissue. In particular, electrical stimulation energy conveyed to the electrodes creates an electrical field, which, when strong enough, depolarizes (or "stimulates") the neural fibers within the spinal cord beyond a threshold level, thereby inducing the firing of action potentials (APs) that propagate along the neural fibers to provide the desired efficacious therapy to the patient.

While SCS has been shown to be successful for neuropathic pain, many patients suffer from musculoskeletal pain arising from muscle disuse atrophy or neuronal muscle control compromise. Ongoing research suggests that the multifidus and multiphanous muscles may be particularly involved with the generation of lower back pain, for example. Rehabilitation programs focus on improving strength of particular muscle groups, but these approaches can involve extensive exercise programs. Such programs may require assistance from physical and occupational therapists, training on the use of gym equipment, and multiple patient visits to the clinic. Thus, there remains a need for a rehabilitation program that can be conducted in the patient's home.

SUMMARY OF THE INVENTION

In accordance with the present inventions, a method for treating a patient requiring conditioning one or more muscle groups using at least one electrode implanted within a ventral epidural space of the patient is provided. The method comprises conveying electrical stimulation energy (e.g., a train of electrical pulses having a pulse width in the range of 20-200 microseconds and a pulse rate in the range of 0.1-30 Hertz) from the implanted electrode(s) to motor efferents (e.g., at a spinal level in the range of T7-L3) respectively innervating the muscle group(s), thereby activating the muscle group(s). Each of muscle groups(s) may comprise, e.g., a plurality of fibers in a muscle fascicle, a plurality of fascicles in a named muscle, a plurality of muscles in a functional muscle unit, a plurality of functional muscle units in a jointed appendage, and a plurality of jointed appendages in an anatomical extremity.

If the patient suffers from musculoskeletal pain, the activation of the muscle group(s) may treat the musculoskeletal pain. If the patient suffers from muscle disuse atrophy, the activation of the muscle group(s) may treat the muscle disuse atrophy. If the patient suffers from neuronal muscle control compromise, the activation of the muscle group(s) may treat the muscle disuse atrophy. The activation of the muscle group(s) may even enhance the performance of the muscle group(s). The muscle groups may be activated when the patient is at rest, in a prescribed position, or exercising.

In one method, the electrode(s) comprises a plurality of electrode sets, the one or more muscle groups comprises a plurality of muscle groups, and the electrical stimulation energy is respectively conveyed from the plurality of electrode sets to the motor efferents respectively innervating the plurality of muscle groups, thereby activating the plurality of muscle groups. Each muscle group may control movement of a jointed appendage, in which case, the electrical stimulation energy may be respectively conveyed from the plurality of electrode sets (e.g., in a respective plurality of timing channels) to the motor efferents respectively innervating the plurality of muscle groups, thereby activating the plurality of muscle groups and moving the jointed appendages.

The electrical stimulation energy may be conveyed from the plurality of electrode sets in accordance with a preset sequence that sequentially activates the plurality of muscle groups at different times. At least two of the of the muscle groups may be antagonistic relative to each other. For example, in one method, a first one of the muscle groups may comprise a calf, a second one of the muscle groups may comprise a quadriceps, a third one of the muscle groups may comprise hamstrings, and a fourth one of the muscle groups may comprise a gluteal maximus. As another example, a first one of the muscle groups comprises a medial gastrocnemius, a second one of the muscle groups comprises a lateral gastrocnemius, and a third one of the muscle groups comprises a soleus.

An optional method further comprises conveying additional electrical stimulation energy from another one or more electrodes implanted within the dorsal epidural space of the patient to sensory afferents respectively innervating the one or more muscle groups, thereby activating the one or more muscle groups via a reflex mechanism.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present invention are obtained, a more particular description of the present invention briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE DRAWINGS

Figure 1:
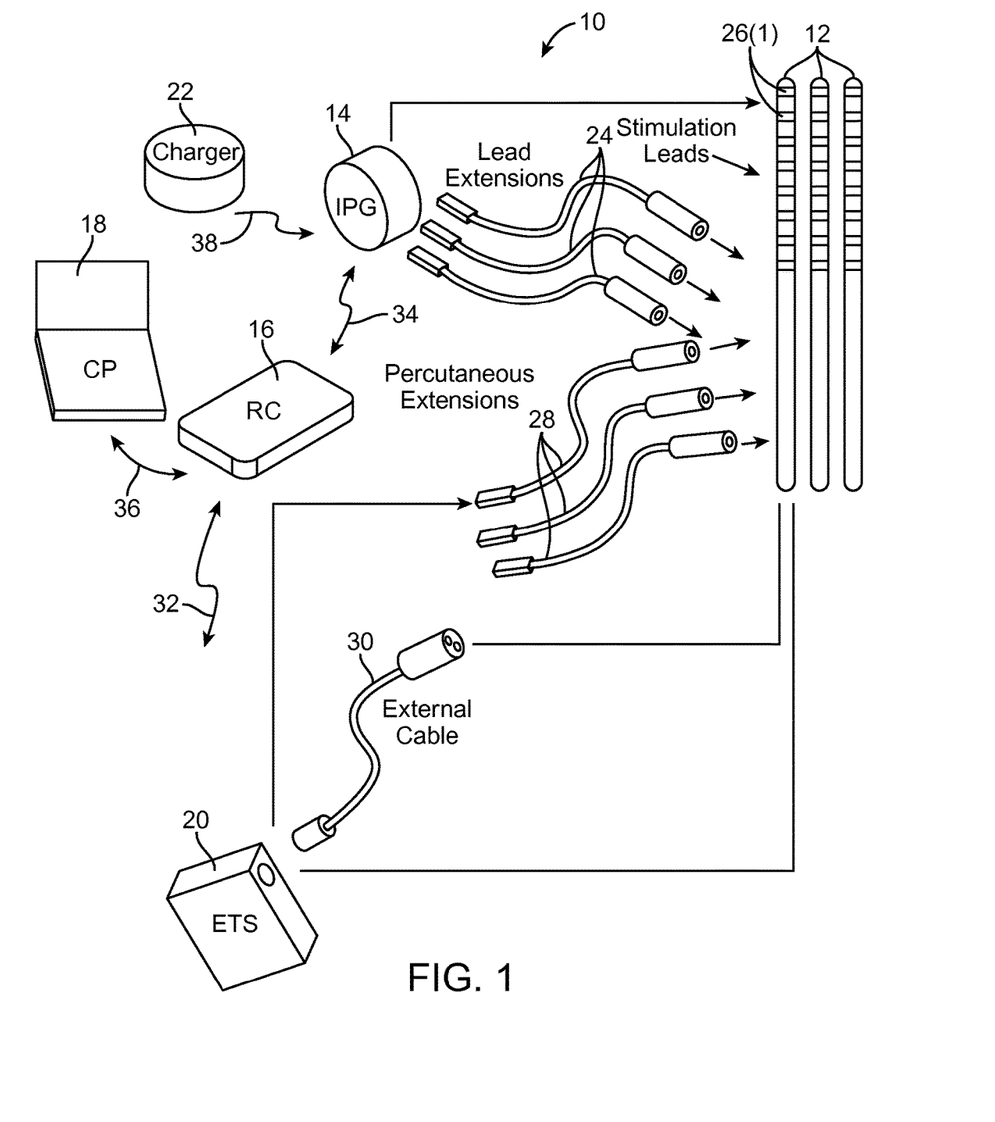
FIG. 1 is a plan view of a Spinal Cord Stimulation (SCS) system constructed in accordance with one embodiment of the present inventions.

Turning first to FIG. 1, an exemplary SCS system 10 generally comprises a plurality of stimulation leads 12 (in this case, three), an implantable pulse generator (IPG) 14 (or alternatively RF receiver-stimulator), an external remote control RC 16, a Clinician's Programmer (CP) 18, an External Trial Stimulator (ETS) 20, and an external charger 22. The IPG 14 is physically connected via one or more lead extensions 24 to the stimulation leads 12, which carry a plurality of electrodes 26 arranged in an array.

The stimulation leads 12 are illustrated as percutaneous leads in FIG. 1, although as will be described in further detail below, a surgical paddle lead can be used in place of the percutaneous leads. As will also be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the neurostimulation leads 12. The ETS 20, which has similar pulse generation circuitry as the IPG 14, also delivers electrical stimulation energy in the form of a pulse electrical waveform to the electrode array 26 accordance with a set of stimulation parameters. The major difference between the ETS 20 and the IPG 14 is that the ETS 20 is a non-implantable device that is used on a trial basis after the neurostimulation leads 12 have been implanted and prior to implantation of the IPG 14, to test the responsiveness of the stimulation that is to be provided. Thus, any functions described herein with respect to the IPG 14 can likewise be performed with respect to the ETS 20.

The RC 16 may be used to telemetrically control the ETS 20 via a bi-directional RF communications link 32. Once the IPG 14 and neurostimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. As will be described in further detail below, the CP 18 provides clinician detailed stimulation parameters for programming the IPG 14 and ETS 20 in the operating room and in follow-up sessions.

The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18).

For purposes of brevity, the details of the RC 16, CP 18, ETS 20, and external charger 22 will not be described herein. Details of exemplary embodiments of these devices are disclosed in U.S. Pat. No. 6,895,280, which is expressly incorporated herein by reference.

Figure 2:
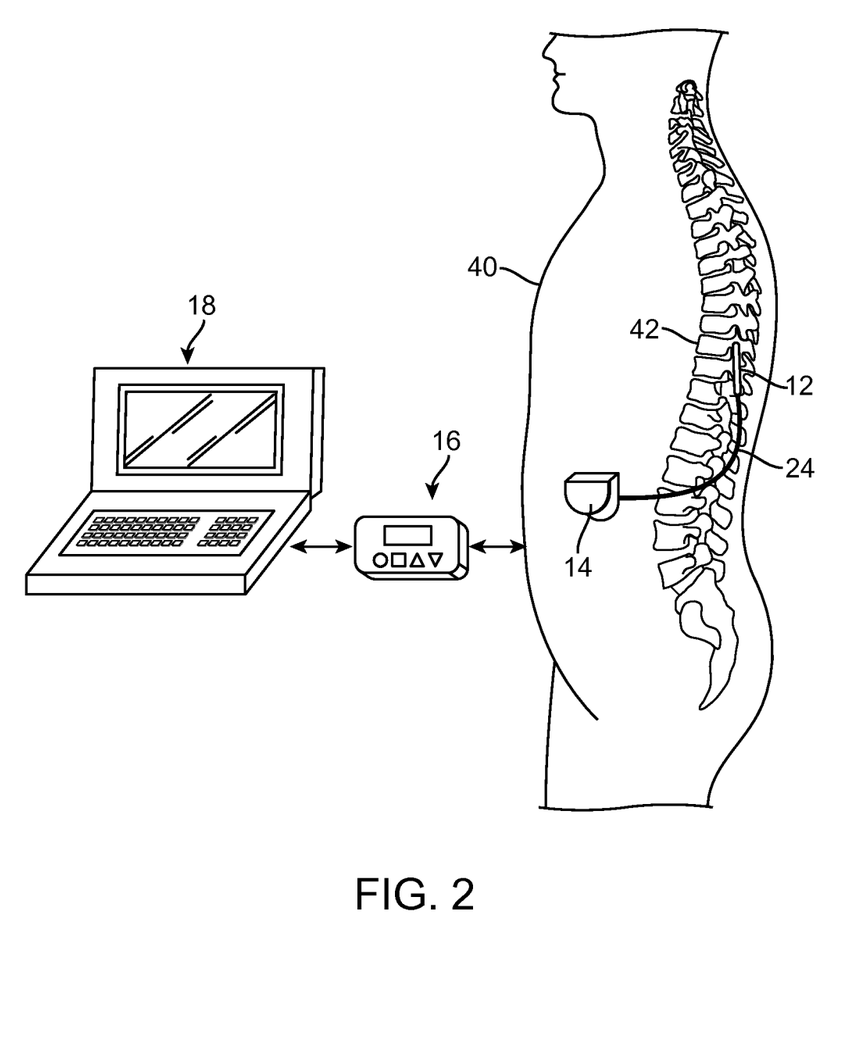
FIG. 2 is a plan view of the SCS system of FIG. 1 in use within a patient.

As shown in FIG. 2, the stimulation leads 12 are implanted within the spinal column 42 of a patient 40. The preferred placement of the electrode leads 12 is adjacent, i.e., resting upon, the spinal cord area to be stimulated. Due to the lack of space near the location where the electrode leads 12 exit the spinal column 42, the IPG 14 is generally implanted in a surgically-made pocket either in the abdomen or above the buttocks. The IPG 14 may, of course, also be implanted in other locations of the patient's body. The lead extensions 24 facilitate locating the IPG 14 away from the exit point of the electrode leads 12. As there shown, the CP 18 communicates with the IPG 14 via the RC 16.

Figure 3:
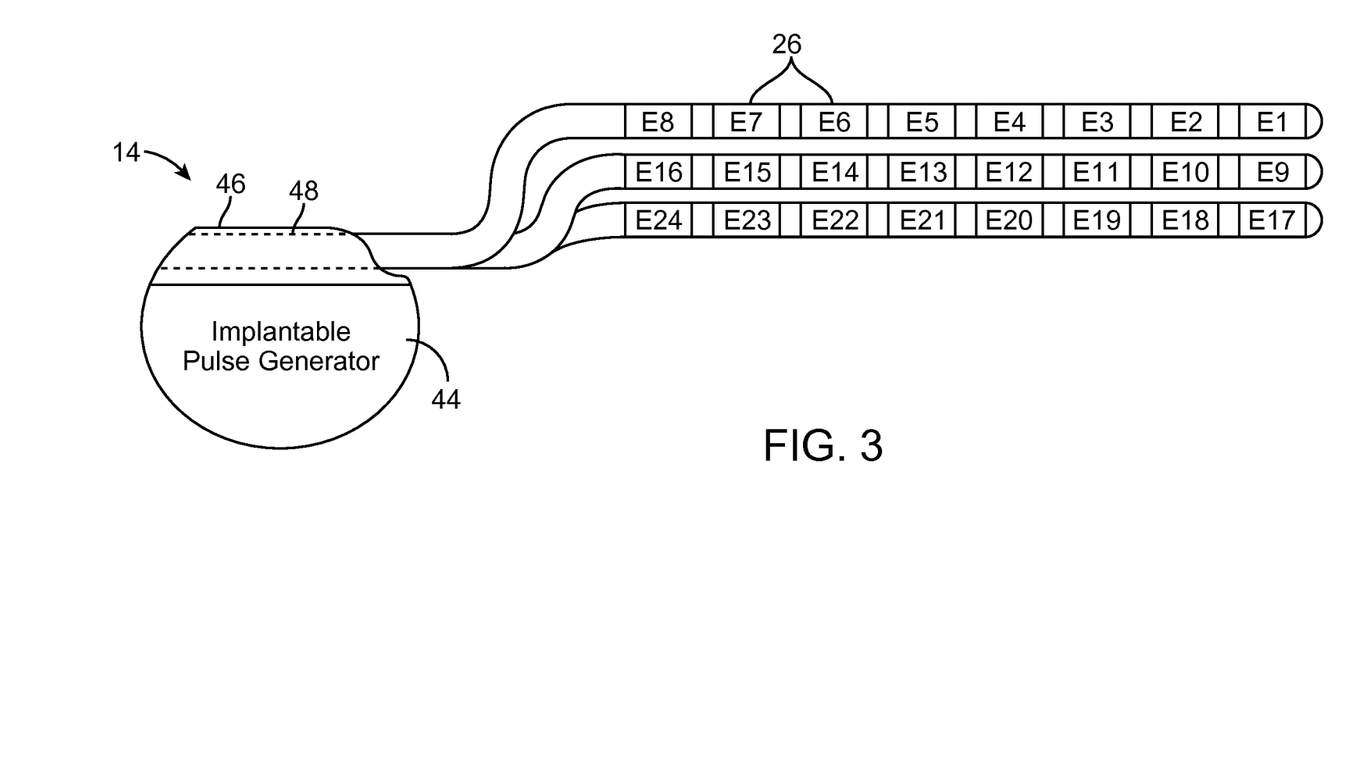
FIG. 3 is a plan view of an implantable pulse generator (IPG) and three percutaneous stimulation leads used in the SCS system of FIG. 1.

Referring now to FIG. 3, the external features of the stimulation leads 12 and the IPG 14 will be briefly described. Each of the stimulation leads 12 has eight electrodes 26 (respectively labeled E1-E8, E9-E16, and E17-E24). The actual number and shape of leads and electrodes will, of course, vary according to the intended application. Further details describing the construction and method of manufacturing percutaneous stimulation leads are disclosed in U.S. Patent Application Ser. No. 11/689,918, entitled "Lead Assembly and Method of Making Same," and U.S. patent application Ser. No. 11/565,547, entitled "Cylindrical Multi-Contact Electrode Lead for Neural Stimulation and Method of Making Same," the disclosures of which are expressly incorporated herein by reference.

Figure 4:
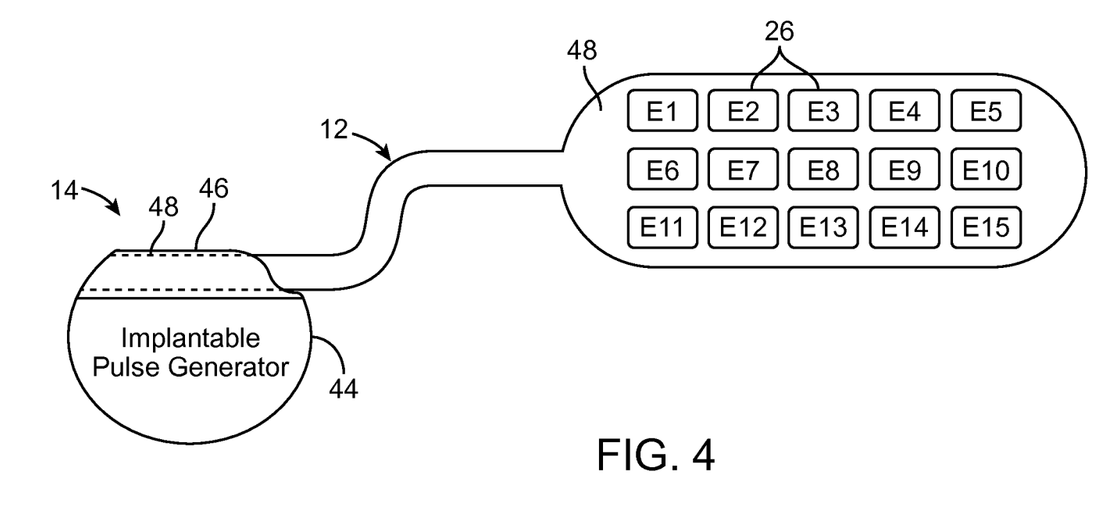
FIG. 4 is a plan view of an implantable pulse generator (IPG) and a surgical paddle lead used in the SCS system of FIG. 1.

Alternatively, as illustrated in FIG. 4, the stimulation lead 12 takes the form of a surgical paddle lead on which electrodes 26 are arranged in a two-dimensional array in three columns (respectively labeled E1-E5, E6-E10, and E11-E15) along the axis of the stimulation lead 12. In the illustrated embodiment, five rows of electrodes 26 are provided, although any number of rows of electrodes can be used. Each row of the electrodes 26 is arranged in a line transversely to the axis of the lead 12. The actual number of leads and electrodes will, of course, vary according to the intended application. Further details regarding the construction and method of manufacture of surgical paddle leads are disclosed in U.S. patent application Ser. No. 11/319,291, entitled "Stimulator Leads and Methods for Lead Fabrication," the disclosure of which is expressly incorporated herein by reference.

In each of the embodiments illustrated in FIGS. 3 and 4, the IPG 14 comprises an outer case 44 for housing the electronic and other components (described in further detail below). The outer case 44 is composed of an electrically conductive, biocompatible material, such as titanium, and forms a hermetically sealed compartment wherein the internal electronics are protected from the body tissue and fluids. In some cases, the outer case 44 may serve as an electrode. The IPG 14 further comprises a connector 46 to which the proximal ends of the stimulation leads 12 mate in a manner that electrically couples the electrodes 26 to the internal electronics (described in further detail below) within the outer case 44. To this end, the connector 46 includes one or more ports (three ports 48 or three percutaneous leads or one port for the surgical paddle lead) for receiving the proximal end(s) of the stimulation lead(s) 12. In the case where the lead extensions 24 are used, the port(s) 44 may instead receive the proximal ends of such lead extensions 24.

The IPG 14 includes pulse generation circuitry that provides electrical conditioning and stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), pulse rate (measured in pulses per second), and burst rate (measured as the stimulation on duration X and stimulation off duration Y).

Electrical stimulation will occur between two (or more) activated electrodes, one of which may be the IPG case 44. Simulation energy may be transmitted to the tissue in a monopolar or multipolar (e.g., bipolar, tripolar, etc.) fashion. Monopolar stimulation occurs when a selected one of the lead electrodes 26 is activated along with the case 44 of the IPG 14, so that stimulation energy is transmitted between the selected electrode 26 and the case 44. Bipolar stimulation occurs when two of the lead electrodes 26 are activated as anode and cathode, so that stimulation energy is transmitted between the selected electrodes 26. For example, an electrode on one lead 12 may be activated as an anode at the same time that an electrode on the same lead or another lead 12 is activated as a cathode. Tri-polar stimulation occurs when three of 15 the lead electrodes 26 are activated, two as anodes and the remaining one as a cathode, or two as cathodes and the remaining one as an anode. For example, two electrodes on one lead 12 may be activated as anodes at the same time that an electrode on another lead 12 is activated as a cathode.

The stimulation energy may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) stimulation pulse and an anodic (positive) recharge pulse that is generated after the stimulation pulse to prevent direct current charge transfer through the tissue, thereby avoiding electrode degradation and cell trauma. That is, charge is conveyed through the electrode-tissue interface via current at an electrode during a stimulation period (the length of the stimulation pulse), and then pulled back off the electrode-tissue interface via an oppositely polarized current at the same electrode during a recharge period (the length of the recharge pulse).

Figure 5:
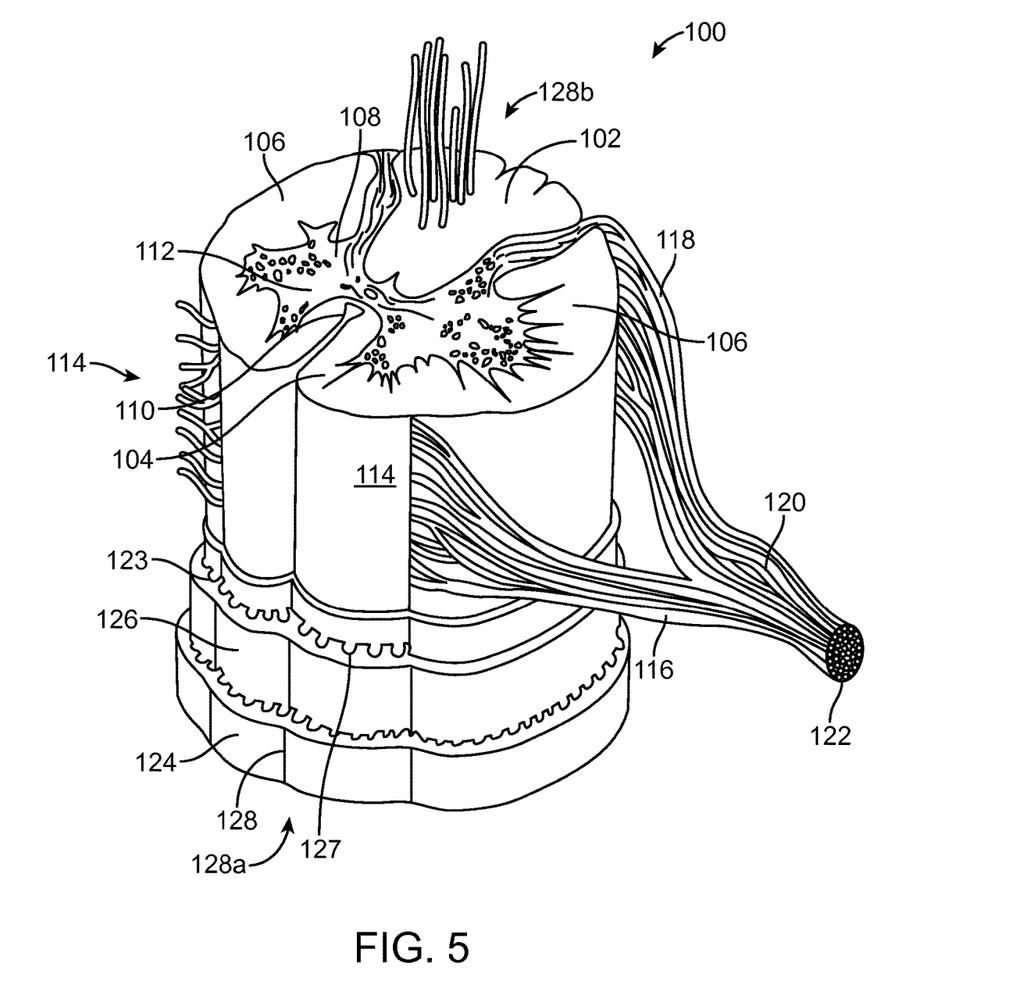
FIG. 5 is a pictorial view of the spinal cord and spinal nerves.
Figure 6:
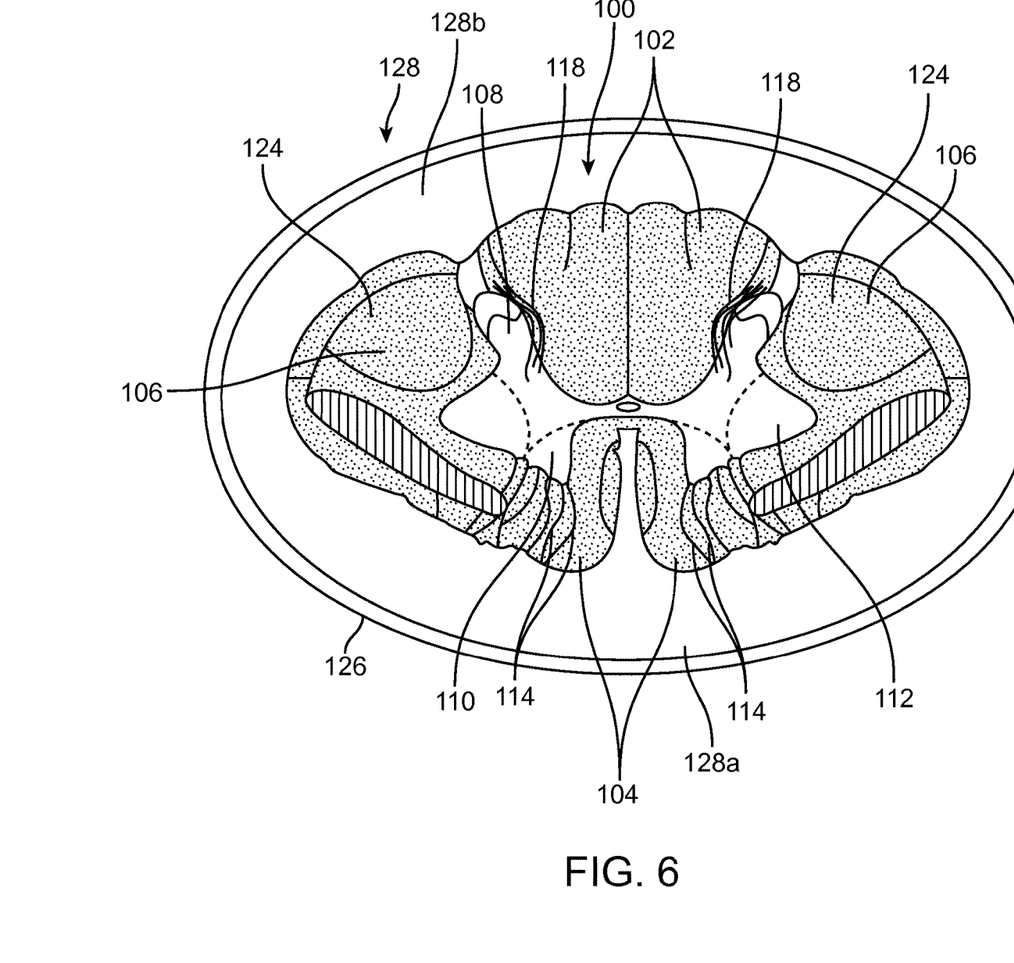
FIG. 6 is a cross-sectional view of the spinal cord.

Referring now to FIGS. 5 and 6, the portions of the spinal cord 100 that are relevant to the present inventions will be described. The spinal cord 100 is divided into three columns: the dorsal column 102, the ventral column 104, and the lateral column 106. Similarly, the butterfly-shaped gray matter of the spinal cord 100 is divided into the dorsal horn 108, the ventral horn 110, and the lateral horn 112.

A group of motor nerve rootlets (ventral root (VR) nerve fibers) 114 branch off of the ventral horn 110 and combine to form the ventral root 116. Similarly, a group of sensory nerve rootlets (dorsal root (DR) nerve fibers) 118 branch off of the dorsal horn 108 and combine to form the dorsal root 120. The dorsal root 120 and the ventral root 116 combine to form the spinal nerve 122, which innervates peripheral regions (e.g., arms, legs, etc.) of the patient's body. It will be noted that symmetrical motor nerve rootlets, ventral root, sensory nerve rootlets, dorsal root, and spinal nerve are located on the opposite side of spinal cord 100, but these elements are omitted for simplicity. A number of spinal nerves branch off the spinal cord. In each patient, there are eight cervical spinal nerves designated C1-C8, twelve thoracic spinal nerves designated T1-T12, five lumbar spinal nerves designated L1-L5, and five sacral spinal nerves designated S1-S5.

The spinal cord 100 is protected by three layers of connective tissue, the dura mater 126, the arachnoid 124, and the pia mater 123, collectively referred to as meninges. Epidural space 128 surrounds the dura mater 126, and sub-arachnoid space 127 lies under the arachnoid 124. The epidural space 128 may be topologically divided into two halves: a ventral epidural space 128a and a dorsal epidural space 128b.

Having described the structure and function of the SCS system 10, various techniques in using the SCS system 10 for treating muscle disuse atrophy and neuronal muscle control compromise and enhancing muscle performance will now be described.

In each of these techniques, one or more of the percutaneous leads and/or the surgical paddle lead 12 illustrated in FIGS. 3 and 4 may be implanted within the epidural space 128. For purposes of simplicity and brevity, the techniques described below use the minimum number of electrodes (in some cases, only one electrode, and in other cases, two electrodes), although additional electrodes may be used.

Figure 7:
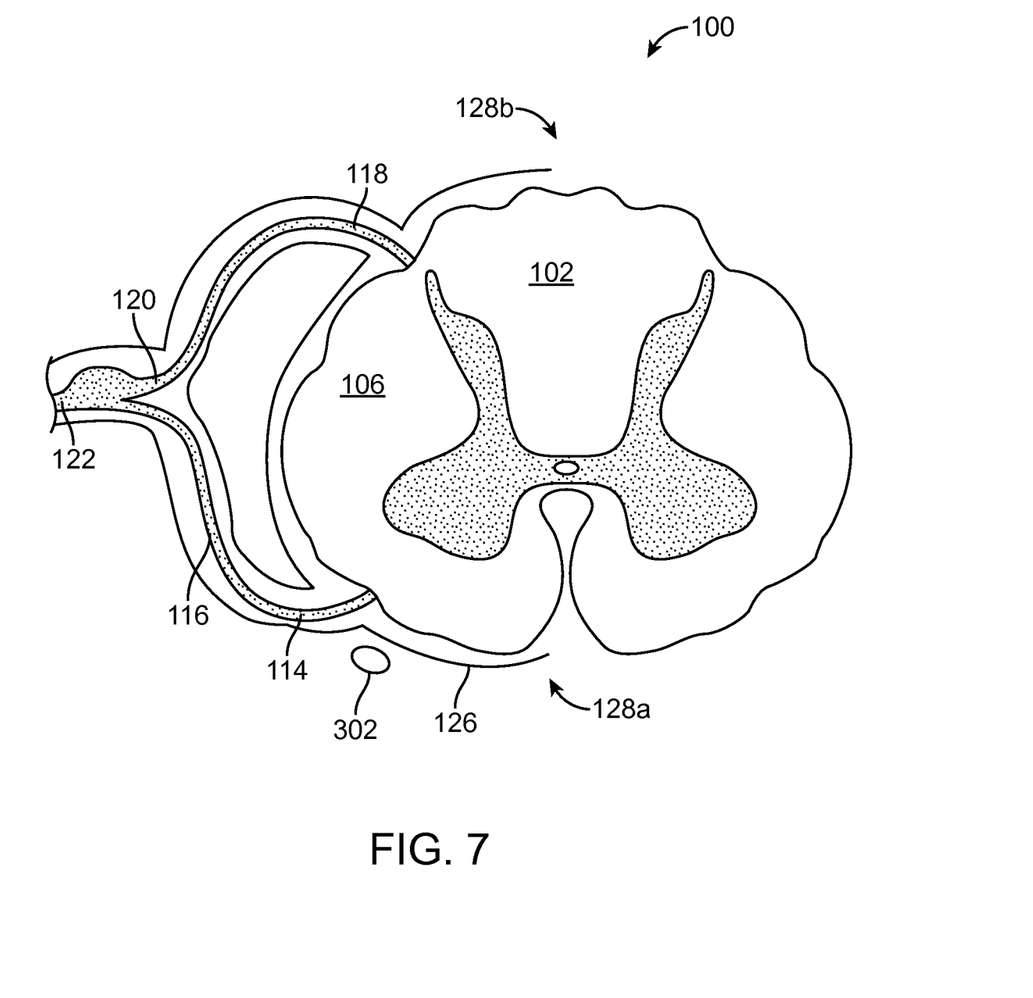
FIG. 7 is a schematic view showing an exemplary single-electrode arrangement relative to the epidural space in accordance with a stimulation regime of the present invention.

Referring to FIG. 7, a preferred embodiment of the present disclosure will be described. There, an electrode 302 is positioned in the ventral epidural space 128a. As explained in more detail below, electrode 302 can comprise a single electrode or electrodes set, carried on a percutaneous lead or a surgical paddle, as described in connection with electrodes 26, above. Conventional SCS techniques apply stimulation to the dorsal column 102 of the spinal cord 100 to treat chronic neuropathic pain. Here, in contrast, the electrode location and the associated stimulation regime are designed to mildly stimulate efferent neural structures, such as, for example, motor nerve rootlets 114 and ventral nerve 116. In this context, mild stimulation is defined as stimulation sufficient to condition one or more muscle groups, designed to enhance muscle performance or response for patients suffering from musculoskeletal pain or for athletes during training. For low back conditioning, optimal locations are generally in or near the T7-L3 vertebral levels.

A brief summary of muscle structure will be helpful at this point. Three types of muscle structure are found in the human body, skeletal, smooth, and cardiac. For purposes of the present invention, skeletal muscles are considered herein. Skeletal muscles are formed of striated muscle tissue under control of the somatic nervous system. These muscles are attached to bones by bundles of collagen fibers known as tendons. Skeletal muscle is made up of individual components known as myocytes, or "muscle cells", sometimes colloquially called "muscle fibers." Fibers are bundled into fascicles, and fascicles in turn form a distinct, or named, muscle, such as, for example, the medial gastrocnemius or the gluteus maximus. Individual muscles cooperate with other muscles in a functional muscle unit, such as the calf muscle. Several such units will be present in a jointed appendage, such as the lower leg and several jointed appendages may form an anatomical extremity, such as an entire leg. It will be further understood that functional muscle units may also be referred to as muscle groups. Examples of muscle groups may include, but are not limited to, calf muscles, quadriceps, hamstrings, gluteus maximii, medial gastrocnemii, lateral gastrocnemii, and soleii. For the purposes of this specification, a group of muscles may comprises a plurality of fibers in a muscle fascicle, a plurality of fascicles in a named muscle, a plurality of muscles in a functional muscle unit, a plurality of functional muscle units in a jointed appendage, or a plurality of jointed appendages in an anatomical extremity.

It will be understood that FIG. 7, as well as the similar figures to follow, schematically illustrate only half of the spinal cord 100. Nerve structures such as dorsal nerve 118 and ventral nerve 116 are found on the opposite side of spinal cord 100 as well. As noted above, electrode 302, and similar electrode representations to follow, is depicted by a single dot, the implanted lead may include one or more individual electrodes in an electrode array, such as that shown for electrodes 26. Hereinafter, the term "electrode set" will be employ to indicate any of the various forms of electrode or electrode array discussed above or known to those in the art, now existing or hereafter developed. For such electrode sets, narrow electrode spacing may allow for maximum control of the stimulation field. The physician may employ that control to tune the stimulated motor fibers to optimize therapeutic effect. Further, similar electrodes or electrodes or electrode sets may be implanted at multiple spinal levels, based on the patient's needs.

Care must be taken, however, to avoid simultaneously stimulating antagonistic muscle groups. Antagonistic muscle groups exert forces on the same skeletal structures, but in different directions. For example, the quadriceps muscle group is antagonistic to the hamstring muscle group. When the quadriceps contracts, the hamstring muscle group relaxes, allowing the leg to flex and extend. Clearly, if stimulation is to be provided to both such muscle groups, stimulation must be applied at different times. Those of skill in the art will understand which muscle groups require particular care to avoid conflicting stimulation.

In the illustrated embodiment, stimulation is delivered at a low rate (0.1-30 Hz) with a relatively brief pulse width (20-200 μs), at an amplitude controlled by a stimulator, such as the IPG 14, selected to create a mild but clear motor sensation. The patient may regulate the IPG 14 to control the overall amplitude that assures comfort and control during stimulation. The IPG 14 may control the stimulation amplitude in a graded fashion for activating muscle groups to varying degrees of recruitment. The degree of muscle recruitment may also be controlled using stimulation rate and pulse width discussed previously. However, it should be noted that higher stimulation rates within the range of 0.1-30 Hz create higher degrees of tetany. Stimulation parameters are set and then adjusted for therapeutic effectiveness and patient comfort.

In one embodiment, the electrical stimulation energy may be conveyed to one or more electrode sets to stimulate motor efferents in a sequence designed to activate associated sets of muscles in a pattern to produce a multi-step physical action, such as, for example, moving a jointed appendage. One embodiment could employ multiple electrode sets to stimulate in turn the calf muscle group, the quadriceps set, the hamstring set, and the gluteus maximus set, causing patient to raise his or her toes, lift and flex her leg, and take a step. Similarly, the system could be programmed to stimulate the medial gastrocnemius set, the lateral gastrocnemius set, and the soleus set, causing the patient to flex his or her lower leg.

Stimulation patterns can be varied for each electrode. In one embodiment, the stimulation can be programmed for delivery either in a continuous train of electrical pulses for a set period of time, such as 5-20 minutes or in bursts, such as 10 pulses ON/20 pulses OFF. In either mode, the electrode set may be spaced for maximum effectiveness, as determined by experimentation, such as on a weekly or daily basis. Best results may be obtained when the patient is still and resting. In addition, desirable results may be achieved when a patient is exercising or is in a prescribed position, for example, when the patient is stretching his arms and legs in opposite directions. Stimulation according to the listed parameters has been observed as sufficient to condition or enhance muscle response.

The muscle groups may be selectively activated through stimulation of efferents innervating those muscles, using multiple stimulation leads such as leads 12. Accordingly, the individual polarity of the contacts on each of the leads 12 may be pre-programmed at a physician's office, for example, using current to shape the fields for particular muscle group control, as well as other parameter variations, discussed above. Each lead may then be sequenced to work the muscle group in a desired fashion, for example, to avoid antagonistic muscle groups from being simultaneously activated for various purposes such as to improve/unload joints that may be stressed due to muscles already in spasm. One novel current steering method is described in U.S. patent application Ser. No. 12/938,282, entitled "System and Method for Mapping Arbitrary Electric Fields to Pre-existing Lead Electrodes," which is expressly incorporated herein by reference.

An alternative embodiment illustrated in FIG. 8 will now be described. As in the embodiment of FIG. 7, a ventral electrode 302, such as the electrode 26, is located in the ventral epidural space 128a near VR 116. In addition, a dorsal electrode 354 is implanted in the dorsal epidural space 128b near sensory nerve rootlets 118 and dorsal root 120. This embodiment may be advantageously employed if electrode 354 had previously been implanted, where, for example, the patient had been receiving spinal cord stimulation treatment. If desired, the two electrodes 302, 354 could be employed from the outset. In that embodiment, ventral electrode 302 could be stimulated according to the regime set out in connection with FIG. 7.

Dorsal electrode 354, however, can also be employed to provide motor stimulation, which may activate sensory afferents by activating dorsal root 120 or dorsal column 102 through reflex facilitation. That stimulation activates the muscle group or groups innervated by the stimulated sensory afferent. The stimulation regime for dorsal electrode 354 can employ parameters similar to those set out for ventral electrode 302. The two electrodes could be programmed and energized separately, or they can interact, sharing current between them. Those of skill in the art will understand the techniques required to manage the stimulation regimes in either embodiment.

Moreover, those of skill in the art will be able to adjust the specific positioning of dorsal electrode 354 to accomplish a desired pattern of stimulation. Ventral electrode 302 remains positioned as discussed in connection with FIG. 7, within epidural space 128, proximate to VR 116.

Figure 8:
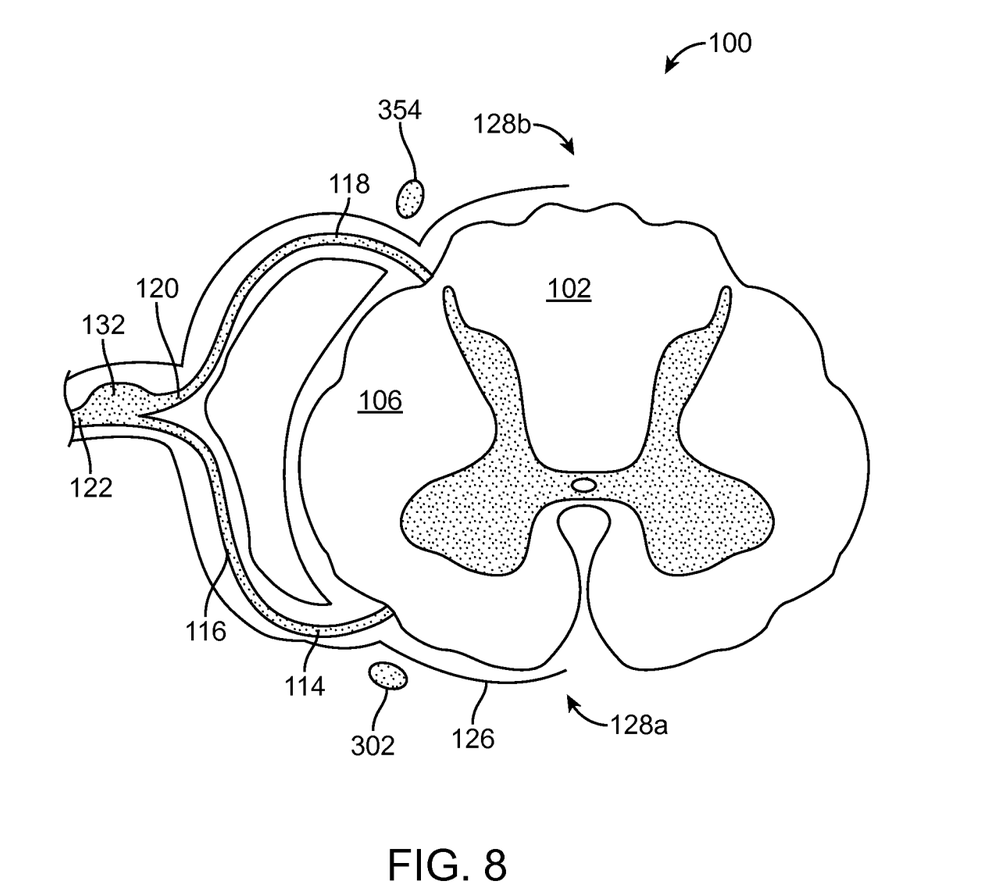
FIG. 8 is a schematic view showing an exemplary double-electrode arrangement relative to the epidural space in accordance with a stimulation regime of the present invention.

In one embodiment, the dorsal electrode 354 may be configured as the cathode, in a monopolar arrangement with the IPG case 44, stimulating the afferent neural structure involved in a particular embodiment, which could be DR 118 (FIG. 8). Ventral electrode 302 can be configured as the cathode, in a manner described above, also in a monopolar arrangement with the IPG case 44, applying stimulation energy to the efferent neural structure, VR 116. Notably, due to the monopolar arrangement, the field strength of the stimulation energy conveyed from the ventral electrode 302 or the dorsal electrode 354, as the case may be, based on above discussion, decays at a relatively low rate with distance. As such, the ventral electrode 302 may be relatively far from the efferent neural structure, VR 116 or the dorsal electrode 354 may be relatively far from the afferent neural structure, DR 118 for modulating the excitability of the efferent neural structure, VR 116 or the afferent neural structure DR 118, respectively.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method for treating a patient requiring conditioning one or more muscle groups using at least one electrode implanted within a ventral epidural space of the patient, the method comprising:
conveying electrical stimulation energy from the at least one implanted electrode to motor efferents respectively innervating the one or more muscle groups, thereby activating the one or more muscle groups.

2. The method of claim 1, wherein the applied electrical stimulation energy comprises a train of electrical pulses.

3. The method of claim 2, wherein each of the applied electrical pulses has a pulse width in the range of 20-200 microseconds.

4. The method of claim 2, wherein the applied electrical pulses have a pulse rate in the range of 0.1-30 Hertz.

5. The method of claim 1, wherein each of the one or more muscle groups comprises one of a plurality of fibers in a muscle fascicle, a plurality of fascicles in a named muscle, a plurality of muscles in a functional muscle unit, a plurality of functional muscle units in a jointed appendage, and a plurality of jointed appendages in an anatomical extremity.

6. The method of claim 1, wherein the at least one electrode comprises a plurality of electrode sets, the one or more muscle groups comprises a plurality of muscle groups, and the electrical stimulation energy is respectively conveyed from the plurality of electrode sets to the motor efferents respectively innervating the plurality of muscle groups, thereby activating the plurality of muscle groups.

7. The method of claim 5, wherein each muscle group controls movement of a jointed appendage, wherein the electrical stimulation energy is respectively conveyed from the plurality of electrode sets to the motor efferents respectively innervating the plurality of muscle groups, thereby activating the plurality of muscle groups and moving the jointed appendages.

8. The method of claim 6, wherein the electrical stimulation energy is respectively conveyed from the plurality of electrode sets to the motor efferents within a plurality of timing channels.

9. The method of claim 6, wherein the electrical stimulation energy is conveyed from the plurality of electrode sets in accordance with a preset sequence that sequentially activates the plurality of muscle groups at different times.

10. The method of claim 9, wherein at least two of the muscle groups are antagonistic relative to each other.

11. The method of claim 9, wherein a first one of the muscle groups comprises a calf, a second one of the muscle groups comprises a quadriceps, a third one of the muscle groups comprises hamstrings, and a fourth one of the muscle groups comprises a gluteal maximus.

12. The method of claim 9, wherein a first one of the muscle groups comprises a medial gastrocnemius, a second one of the muscle groups comprises a lateral gastrocnemius, and a third one of the muscle groups comprises a soleus.

13. The method of claim 1, wherein the one or more motor afferents are at a spinal level in the range of T7-L3.

14. The method of claim 1, further comprising conveying additional electrical stimulation energy from another one or more electrodes implanted within the dorsal epidural space of the patient to sensory afferents respectively innervating the one or more muscle groups, thereby activating the one or more muscle groups via a reflex mechanism.

15. The method of claim 1, wherein the patient suffers from musculoskeletal pain, and the activation of the one or more muscle groups treats the musculoskeletal pain.

16. The method of claim 1, wherein the patient suffers from muscle disuse atrophy, and the activation of the one or more muscle groups treats the muscle disuse atrophy.

17. The method of claim 1, wherein the patient suffers from neuronal muscle control compromise, and the activation of the one or more muscle groups treats the muscle disuse atrophy.

18. The method of claim 1, wherein the activation of the one or more muscle groups enhances the performance of the one or more muscle groups.

19. The method of claim 1, wherein the one or more muscle groups are activated when the patient is at rest.

20. The method of claim 1, wherein the one or more muscle groups are activated when the patient is in a prescribed position.

21. The method of claim 1, wherein the one or more muscle groups are activated when the patient is exercising.

* * * * *